United States Patent
Adin et al.

(10) Patent No.: US 7,208,485 B2
(45) Date of Patent: *Apr. 24, 2007

(54) CRYSTALLINE FORMS OF HALOBETASOL PROPIONATE

(75) Inventors: Itai Adin, Beer Sheva (IL); Yuri Futerman, Beer Sheva (IL); Ori Lerman, Givatayim (IL); Alexander Weisman, Kiryat Ekron (IL); Chaim Ashkenazi, Yeruham (IL); Joseph Kaspi, Givatayim (IL)

(73) Assignee: Chemagis Ltd., Bnei Brak (IL)

( * ) Notice: Subject to any disclaimer, the term of this patent is extended or adjusted under 35 U.S.C. 154(b) by 402 days.

This patent is subject to a terminal disclaimer.

(21) Appl. No.: 10/341,690

(22) Filed: Jan. 13, 2003

(65) Prior Publication Data

US 2004/0138191 A1    Jul. 15, 2004

(51) Int. Cl.
*A61K 31/56* (2006.01)
*C07J 7/00* (2006.01)

(52) U.S. Cl. ............... 514/179; 514/180; 552/569; 552/570

(58) Field of Classification Search .......... 514/180, 514/169, 170, 179, 181, 182; 552/569, 570
See application file for complete search history.

(56) References Cited

U.S. PATENT DOCUMENTS

| | | | |
|---|---|---|---|
| 4,113,680 A | 9/1978 | Kamano et al. | |
| 4,273,770 A * | 6/1981 | Alvarez | 514/174 |
| 4,361,558 A | 11/1982 | Wieland | |
| 4,377,575 A | 3/1983 | Stache et al. | |
| 4,619,921 A | 10/1986 | Kalvoda et al. | |
| 4,918,065 A | 4/1990 | Stindl et al. | |
| 5,326,566 A | 7/1994 | Parab | |
| 5,972,920 A | 10/1999 | Seidel | |
| 6,096,731 A | 8/2000 | McDonald | |
| 6,517,847 B2 * | 2/2003 | Dow et al. | 424/401 |
| 6,645,528 B1 * | 11/2003 | Straub et al. | 424/489 |
| 6,656,928 B1 * | 12/2003 | McCadden | 514/167 |
| 6,663,848 B2 * | 12/2003 | Schiewe et al. | 424/46 |
| 6,673,374 B2 * | 1/2004 | Murad | 424/616 |
| 2001/0007083 A1 | 7/2001 | Roorda | |

OTHER PUBLICATIONS

Brittain, H.G., Polymorphism in pharmaceutical solid, drugs and the pharmaceutical sciences, vol. 95, 1999, chapter 6, pp. 227-230 and 232-240.*
Brittain, H.G., P., Polymorphism in pharmaceutical solid, Drugs and the pharmaceutical sciences, vol. 95, 1999, chapter 6, pp. 348-355).*
Ultravete Product Information by Bristol Myers Squibb, Revised Apr. 2003.*
Gutman, Daniella et al., DN 145:426015 CAPLUS, abstract of WO 2006110534.*

* cited by examiner

*Primary Examiner*—Sabiha N. Qazi
(74) *Attorney, Agent, or Firm*—Leydig, Voit & Mayer, Ltd.

(57) ABSTRACT

The present invention provides a crystalline halobetasol propionate selected from the group consisting of halobetasol propionate having crystalline Form I characterized by power X-ray diffraction peak positions and intensities as set forth in Table 1 herein, halobetasol propionate having crystalline Form II characterized by power X-ray diffraction peak positions and intensities as set forth in Table 2 herein, halobetasol propionate having crystalline Form III characterized by power X-ray diffraction peak positions and intensities as set forth in Table 3 herein, halobetasol propionate having crystalline Form IV characterized by power X-ray diffraction peak positions and intensities as set forth in Table 4 herein, halobetasol propionate having crystalline Form V characterized by power X-ray diffraction peak positions and intensities as set forth in Table 5 herein, and halobetasol propionate having crystalline Form VI characterized by power X-ray diffraction peak positions and intensities as set forth in Table 6 herein.

36 Claims, 18 Drawing Sheets

CRYSTALLINE FORMS OF HALOBETASOL PROPIONATE

FIELD OF THE INVENTION

The present invention relates to new crystalline forms of halobetasol propionate, and processes for their preparation and stable topical pharmaceutical compositions based thereon.

BACKGROUND OF THE INVENTION

The trihalogenated corticosteroid halobetasol propionate of the formula

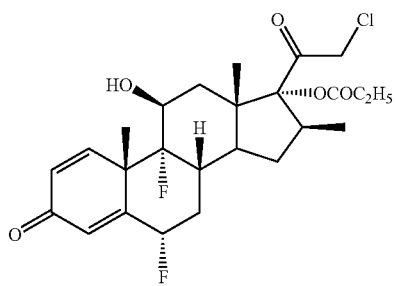

also known as ulobetasol propionate is (6α, 9α, 11β, 16β, 17α)-21-Chloro-6,9-difluoro-11-hydroxy-16-methyl-17-(1-oxopropoxy)pregna-1,4-diene-3,20-dione.

Halobetasol propionate has been described in U.S. Pat. No. 4,619,921 as a new topical polyhalogenated corticosteroid, presenting topical anti-inflammatory activity, whilst having low systemic activity. Halobetasol propionate is marketed in the U.S. as Ultravate® cream and Ultravate® ointment. It is indicated for the relief of the inflammatory and pruritic manifestations of corticosteroid-responsive dermatoses.

The search for new crystalline forms is relevant to the pharmaceutical sciences, since different crystalline forms of the same drug can possess different dissolution profile, pharmacokinetic profile and stability properties. The discovery of a new crystalline form of a drug provides an opportunity to improve its performance—it broadens the repertoire of materials that a formulation scientist has available for designing, for example, a specific release profile.

The Ultravate products contain only one, yet uncharacterized, crystalline form. The efficacy and safety of other crystalline forms was heretofore unknown. The new crystalline forms are obtained economically, in very good yields via convenient processes and exhibit good stability. Most of the solvents used for their preparation (unlike those described in U.S. Pat. No. 4,619,921) are safe and allow easy handling.

We have now surprisingly found that the new crystalline forms can be formulated in stable topical pharmaceutical compositions with similar or better efficacy than the marketed Ultravate® products.

In addition, the new crystalline forms exhibited excellent solubility and handling properties, allowing for a convenient pharmaceutical manufacturing process. They can be easily suspended or solubilized in the usual pharmaceutical ingredients.

Halobetasol propionate is described in the Merck Index and in U.S. Pat. No. 4,619,921 as being crystallized from methylene chloride/ether and having a melting point of 220–221° C. The exact proportions of the two solvents were not given. Precise characterization of the above mentioned crystalline form of halobetasol propionate, using methods well known to those skilled in the art (powder X-ray diffraction, differential scanning calorimetry, infra-red spectroscopy, etc.) and the exact process for their preparation, is not given. There is no documented evidence that characterizes any crystalline form other than the melting point given in U.S. Pat. No. 4,619,921.

The present invention provides six new crystalline forms of halobetasol propionate and processes for preparing them and stable topical pharmaceutical compositions containing the above crystalline forms.

SUMMARY OF THE INVENTION

The present invention provides new crystalline forms I–VI of halobetasol propionate, and processes for preparing them. Each of the new forms is differentiated by a unique powder X-ray diffraction pattern, and a unique infra-red spectrum.

A general technique that leads to the discovery of a novel crystalline form of a compound may be well known to those skilled in the art. Such techniques include crystallization, thermal treatment, and sublimation. Those skilled in the art appreciate that in the search for new polymorphic forms of a compound, any one of these techniques may fail to provide a new crystalline form of the compound. The search is an empirical exercise that involves trial and error experiments with different techniques and conditions. For these reasons, it is impossible to define all techniques and conditions that will produce halobetasol propionate Forms I–VI. It is, however, possible to provide methods which have successfully and selectively produced halobetasol propionate in one of these desired forms.

The novel crystalline forms of halobetasol propionate have been characterized by powder X-ray diffraction spectroscopy, which produces a fingerprint of the particular crystalline form. Measurements of 2θ values typically are accurate to within ±0.2 degrees.

X-ray diffraction data were acquired using a PHILIPS X-ray diffractometer model PW1050-70. System description: Kα1=1.54178?, voltage 40 kV, current 28 mA, diversion slit=1°, receiving slit=0.2 mm, scattering slit=1° with a Graphite monochromator. Experiment parameters: pattern measured between 2θ=4° and 2θ=30° with 0.05° increments; count time was 0.5 second per increment The novel crystalline forms of halobetasol propionate have been further characterized by infra-red spectroscopy, which is directly related to the local environment around functional groups of a molecule. Different crystalline forms of the same compound can sometimes offer different environments around the molecule's functional groups, and/or different conformations of the molecule. These changes in local environment are mirrored in the Infra-red spectra of the various forms of halobetasol propionate.

Infra-red spectra were acquired using Nicolet Fourrier-transform infra-red spectrometer model Avatar 360, with Omnic software version 5.2. All samples were run as Nujol® mulls. The current infra-red measurements are accurate to within 4 $cm^{-1}$.

Differential scanning calorimetry experiments were run on DuPont instruments model DSC 910, with software version 4.1C. Samples were analyzed inside 40 µl crimped Aluminum pan. Heating rate for all samples was 5° C./min.

Since the melting of halobetasol propionate is accompanied by decomposition, the heating process was stopped slightly after the beginning of melting, in order to avoid damage to the measuring apparatus caused by decomposition products.

The novel forms of halobetasol propionate will now be described in more detail and with reference to the tables incorporated herein in which:

Table 1 represents powder X-ray diffraction peak positions and intensities of halobetasol propionate Form I.

Table 2 represents powder X-ray diffraction peak positions and intensities of halobetasol propionate Form II.

Table 3 represents powder X-ray diffraction peak positions and intensities of halobetasol propionate Form III.

Table 4 represents powder X-ray diffraction peak positions and intensities of halobetasol propionate Form IV.

Table 5 represents powder X-ray diffraction peak positions and intensities of halobetasol propionate Form V.

Table 6 represents powder X-ray diffraction peak positions and intensities of halobetasol propionate Form VI.

Halobetasol Propionate Form I

The present invention provides halobetasol propionate Form I. Form I produces a unique powder X-ray diffraction pattern (Table 1, FIG. 1). The strong reflections at 11.6, 14.5, 18.1, 22.3, 23.0±0.2 degrees 2θ are most characteristic of this form. Form I can be prepared by crystallization from methylene chloride:diethylether mixture (5:1), and can be separated conventionally from the solvent by filtering or decanting.

TABLE 1

Form I
Powder X-ray diffraction peak positions and intensities

| Relative Intensity (%) | Peak Position (2θ deg) |
|---|---|
| 20.4 | 9.9 |
| 21.2 | 11.0 |
| 100.0 | 11.6 |
| 32.1 | 13.6 |
| 30.9 | 14.0 |
| 95.3 | 14.5 |
| 32.5 | 15.1 |
| 42.4 | 16.9 |
| 46.3 | 17.9 |
| 78.5 | 18.1 |
| 29.8 | 19.9 |
| 23.6 | 21.1 |
| 40.5 | 21.3 |
| 31.5 | 21.7 |
| 83.1 | 22.3 |
| 59.3 | 22.6 |
| 70.9 | 23.0 |
| 33.3 | 23.4 |
| 16.6 | 23.7 |
| 26.5 | 24.5 |
| 25.3 | 24.7 |
| 12.5 | 25.4 |
| 42.2 | 25.9 |
| 28.6 | 26.2 |
| 15.0 | 26.9 |
| 19.1 | 28.0 |
| 8.9 | 28.6 |
| 13.5 | 29.4 |

Form I is a solvate, containing around 9% (w/w) of methylene chloride. Weight loss around 90–100° C. was detected by thermogravimetry analysis (TGA), and the identity of the released solvent was independently determined using GC equipped with head-space accessory.

Apparently, this solvent loss is part of an irreversible solid-solid phase transition of Form I to Form III, accompanied by release of the methylene chloride. Upon heating to 90° C., this transition is completed after few minutes.

This transformation was observed visually using hot-stage microscopy, and it also appears as an endothermic peak in differential scanning calorimetry (DSC, FIG. 13).

Form I produces a unique infra-red spectrum (FIG. 7). The pattern created by the peaks at 1607, 1627, 1666, 1715, 1733±4 cm$^{-1}$ is most characteristic of this form.

Surprisingly, halobetasol propionate Form I, obtained by crystallization from the same pair of solvents as the Form mentioned in U.S. Pat. No. 4,619,921, although not necessarily in the same proportions. However, since the literature does not mention any transition and/or weight loss such as observed in Form I, these two Forms (our Form I and the form described in U.S. Pat. No. 4,619,921) should be looked upon as two individual crystalline forms of halobetasol propionate.

Halobetasol Propionate Form II

The present invention provides halobetasol propionate Form II. Form II produces a unique powder X-ray diffraction pattern (Table 2, FIG. 2). The strong reflections at 10.2, 13.0, 14.9, 16.1, 21.0 ±0.2 degrees 2θ are most characteristic of this Form. Form II may be prepared by crystallization from Toluene, and can be separated conventional from the solvent by filtering or decanting.

TABLE 2

Form II
Powder X-ray diffraction peak positions and intensities

| Relative Intensity (%) | Peak Position (2θ deg) |
|---|---|
| 28.5 | 8.0 |
| 100 | 10.2 |
| 28.0 | 11.4 |
| 71.2 | 13.0 |
| 73.7 | 14.9 |
| 78.9 | 16.1 |
| 47.7 | 17.1 |
| 55.1 | 18.2 |
| 15.4 | 19.6 |
| 77.1 | 21.0 |
| 23.5 | 22.0 |
| 38.3 | 22.3 |
| 37.0 | 23.1 |
| 29.4 | 24.1 |
| 53.7 | 25.0 |
| 15.5 | 25.9 |
| 20.6 | 27.3 |
| 15.3 | 28.2 |
| 20.1 | 28.5 |
| 8.8 | 29.0 |

Form II can also be prepared by heating Form V to 90° C. or heating Form VI to 175° C.

Melting range of Form II: 214.5–215.0° C. with consequent decomposition.

DSC of Form II (FIG. 14) showed only one endothermic peak that corresponds to its melting and consequent decomposition.

Form II has been heated at temperatures as high as 200° C. without converting to another crystalline or amorphous form and without undergoing significant decomposition. Hot stage microscopy analysis of Form II showed no detectable transitions upon heating to its melting temperature.

Halobetasol propionate Form II produces a unique infrared spectrum (FIG. 8).

The pattern created by the strong peaks at 1607, 1618, 1662 and 1723±4 cm$^{-1}$ is most characteristic of this form.

Halobetasol Propionate Form III

The present invention provides halobetasol propionate Form III. Form III produces a unique powder X-ray diffraction pattern (Table 3, FIG. 3). The strong reflections at 13.0, 13.5, 14.6 and 23.6±0.2 degrees 2θ are most characteristic of this form.

TABLE 3

Form III
Powder X-ray diffraction peak positions and intensities

| Relative Intensity (%) | Peak Position (2θ deg) |
|---|---|
| 4.2 | 7.0 |
| 42.2 | 10.1 |
| 31.5 | 11.7 |
| 100.0 | 13.0 |
| 85.1 | 13.5 |
| 79.6 | 14.6 |
| 41.8 | 15.1 |
| 20.1 | 15.5 |
| 27.5 | 16.2 |
| 51.7 | 16.5 |
| 52.5 | 17.7 |
| 40.4 | 18.7 |
| 38.9 | 19.0 |
| 43.1 | 20.0 |
| 32.5 | 20.2 |
| 12.4 | 21.6 |
| 35.5 | 22.3 |
| 15.4 | 22.6 |
| 67.4 | 23.6 |
| 46.0 | 24.4 |
| 19.7 | 24.9 |
| 15.5 | 25.3 |
| 30.3 | 26.4 |
| 43.6 | 26.9 |
| 17.1 | 27.5 |
| 32.6 | 30.3 |

Form III may be prepared by crystallization from isopropanol, methylene chloride, or acetone, and it can be separated from the solvent conventionally by filtering or decanting.

Halobetasol propionate Form III can also be prepared by heating Form I to about 90° C. or heating Form IV to 120° C.

Melting range of Form III: 205.8–209.0° C., with consequent decomposition.

Upon heating to 160° C., Form III undergoes a reversible solid-solid phase transition to an unknown form, without any weight loss. This transition was observed visually using hot-stage microscopy, and it also appears as an endothermic peak in DSC (FIG. 15). After cooling back to room temperature, the powder X-ray diffraction pattern of the heated material was identical to that of the starting material.

Form III has a unique infra-red spectrum (FIG. 9). The pattern created by the strong peaks at 1611, 1627, 1665, 1708 and 1742±4 cm$^{-1}$ is particularly characteristic of this form.

Halobetasol Propionate Form IV

The present invention provides halobetasol propionate Form IV. Form IV produces a unique powder X-ray diffraction pattern (Table 4, FIG. 4). The strong reflections at 9.4, 12.8, 13.1 and 19.1±0.2 degrees 2θ are most characteristic of this form. Form IV may be prepared by crystallization from methanol:water (5:1) mixture, and can be separated conventionally from the solvent by filtering or decanting.

TABLE 4

Form IV
Powder X-ray diffraction peak positions and intensities

| Relative Intensity (%) | Peak Position (2θ deg) |
|---|---|
| 9.7 | 6.7 |
| 60.9 | 9.4 |
| 32.1 | 11.5 |
| 81.5 | 12.8 |
| 100.0 | 13.1 |
| 48.5 | 13.6 |
| 49.0 | 13.8 |
| 22.7 | 14.5 |
| 32.2 | 14.8 |
| 55.5 | 15.1 |
| 43.1 | 15.4 |
| 13.2 | 17.4 |
| 43.1 | 18.3 |
| 39.1 | 18.6 |
| 66.2 | 19.1 |
| 25.5 | 19.7 |
| 21.5 | 20.7 |
| 26.8 | 20.9 |
| 59.2 | 21.5 |
| 19.2 | 22.8 |
| 13.6 | 23.6 |
| 40.5 | 24.0 |
| 25.3 | 24.4 |
| 19.8 | 24.7 |
| 2.4 | 25.2 |
| 8.8 | 25.6 |
| 39.2 | 26.4 |
| 12.3 | 26.7 |
| 34.7 | 27.2 |
| 32.6 | 28.2 |
| 35.4 | 28.7 |
| 19.7 | 28.9 |

The exact nature of Form IV is not completely clear. Samples dried at about 50° C. showed the material to contain water and methanol. Weight loss of about 7–10% (w/w) was detected by thermogravimetry (TGA). The identity of the released solvents was independently determined using GC equipped with head-space accessory and Karl Fischer titration.

Apparently, this solvent loss is part of an irreversible solid-solid phase transition of Form IV to Form III, accompanied by release of the solvents. Upon heating to about 120–130° C., this transition is completed after few minutes. This transition was observed visually by hot-stage microscopy, and it also appears as an endothermic peak in DSC (FIG. 16). The same transition can be accomplished by heating Form IV under vacuum at about 60° C. for about an hour or two.

Form IV has a unique infra-red spectrum (FIG. 10). The patterns created by the strong peaks at 1606, 1621, 1664, 1711 and 1727±4 cm$^{-1}$, and three broad hydroxy absorption peaks at 3304, 3425 and 3580±4 cm$^{-1}$ are particularly characteristic of this form.

Halobetasol Propionate Form V

The present invention provides halobetasol propionate Form V. Form V crystallizes concomitantly with Form II by crystallization from ethyl acetate. The powder X-ray diffraction pattern of Form V can be differentiated by subtraction of the diffraction pattern of Form II from that of the mixture. Hence, Form V produces a unique powder X-ray diffraction pattern with reflections at 7.2, 8.5, 9.0, 9.5, 10.8, 14.0, 14.3, 15.3, 15.6, 16.2, 16.9, 17.7, 19.0, 20.1, 21.5, 22.9, 23.5, 23.6, 24.4, 25.4, 26.0, 26.9, 27.2, and 29.5±0.2 degrees 2θ (Table 5, FIG. 5).

TABLE 5

Form V
Powder X-ray diffraction peak positions and intensities

| Relative Intensity (%) | Peak Position (2θ deg) |
| --- | --- |
| 39.5 | 7.2 |
| 3.8 | 8.5 |
| 16.9 | 9.0 |
| 72.1 | 9.5 |
| 6.3 | 10.8 |
| 85.1 | 14.0 |
| 62.6 | 14.3 |
| 49.4 | 15.3 |
| 95.0 | 15.6 |
| 34.5 | 16.2 |
| 38.1 | 16.9 |
| 12.7 | 17.7 |
| 100.0 | 19.0 |
| 18.3 | 20.1 |
| 52.8 | 21.5 |
| 30.0 | 22.9 |
| 26.0 | 23.5 |
| 20.2 | 23.6 |
| 27.8 | 24.4 |
| 14.0 | 25.4 |
| 30.5 | 26.0 |
| 12.3 | 26.9 |
| 14.2 | 27.2 |
| 23.9 | 29.5 |

Form V is a solvate, containing ethylacetate. Weight loss of 4.4% (w/w) around 90–100° C. was detected by thermogravimetric analysis (TGA) of the mixture of the two forms. The identity of the released solvent was independently determined using GC equipped with head-space accessory.

Apparently, this solvent loss is part of an irreversible solid-solid phase transition of Form V to Form II, accompanied by release of the ethyl acetate. Upon heating to about 90° C., this transition is completed after few minutes. This transition was observed visually by hot-stage microscopy, and it also appears as an endothermic peak in DSC (FIG. 17). Farther heating produced a plateau followed by melting and consequent decomposition at around 211–212° C.

The existence of Form V can also be identified by infra-red spectroscopy (FIG. 11). The two peaks around 960±4 cm$^{-1}$ and the unique pattern around 1190 and 1300±4 cm$^{-1}$ can point to the presence of Form V.

Halobetasol Propionate Form VI

The present invention provides halobetasol propionate Form VI. Form VI produces a unique powder X-ray diffraction pattern (Table 6, FIG. 6). The strong reflections at 9.7, 11.3, 12.6, 14.8, 15.7±0.2 degrees 2θ are particularly characteristic of this Form. Form VI can be prepared by crystallization from methanol and can be separated conventionally from the solvent by filtering or decanting.

TABLE 6

Form VI
Powder X-ray diffraction peak positions and intensities

| Relative Intensity (%) | Peak Position (2θ deg) |
| --- | --- |
| 38.7 | 8.5 |
| 25.8 | 9.2 |
| 88.0 | 9.7 |
| 10.0 | 10.0 |
| 61.7 | 11.3 |
| 43.6 | 11.6 |
| 75.9 | 12.6 |
| 47.6 | 13.0 |
| 27.7 | 13.4 |
| 40.6 | 13.9 |
| 100.0 | 14.8 |
| 49.0 | 15.3 |
| 65.2 | 15.7 |
| 43.6 | 16.0 |
| 9.3 | 16.4 |
| 19.2 | 16.9 |
| 35.6 | 17.2 |
| 40.3 | 17.6 |
| 26.9 | 18.2 |
| 29.0 | 18.5 |
| 6.3 | 19.4 |
| 31.5 | 19.8 |
| 32.9 | 20.0 |
| 29.1 | 20.4 |
| 8.0 | 21.2 |
| 14.6 | 21.4 |
| 9.5 | 22.3 |
| 17.9 | 22.5 |
| 16.0 | 22.9 |
| 27.9 | 23.4 |
| 46.2 | 23.8 |
| 24.6 | 24.3 |
| 7.7 | 24.4 |
| 18.9 | 25.1 |
| 19.9 | 25.3 |
| 17.9 | 25.5 |
| 24.1 | 25.9 |
| 28.0 | 26.2 |
| 28.3 | 26.7 |
| 19.9 | 27.2 |

Upon heating to around 150–170° C., Form VI undergoes an irreversible solid-solid phase transition to Form II. DSC of Form VI (FIG. 18) showed a shallow endothermic peak that started around 60° C., and ended at around 120° C. A second endothermic peak started at around 150° C., followed by an exothermic peak that started around 160° C. and ended at around 180°C.

Analysis of Form VI by hot-stage microscopy showed a prolonged transition that started around 60° C. and ended around 160–170° C.

Form VI produces a unique infra-red spectrum (FIG. 12). The pattern created by the peaks at 1600, 1614, 1623, 1633, 1664, 1725 and 1735±4 cm$^{-1}$ and the occurrence of both free and associated hydroxyl peaks at 3659 and 3378±4 cm$^{-1}$ respectively, are most characteristic of this form.

While the invention will now be described in connection with certain preferred embodiments in the following examples and with reference to the attached figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

IN THE DRAWINGS

EXAMPLES

Example 1

Preparation of Halobetasol Propionate Form I

Figure 1:
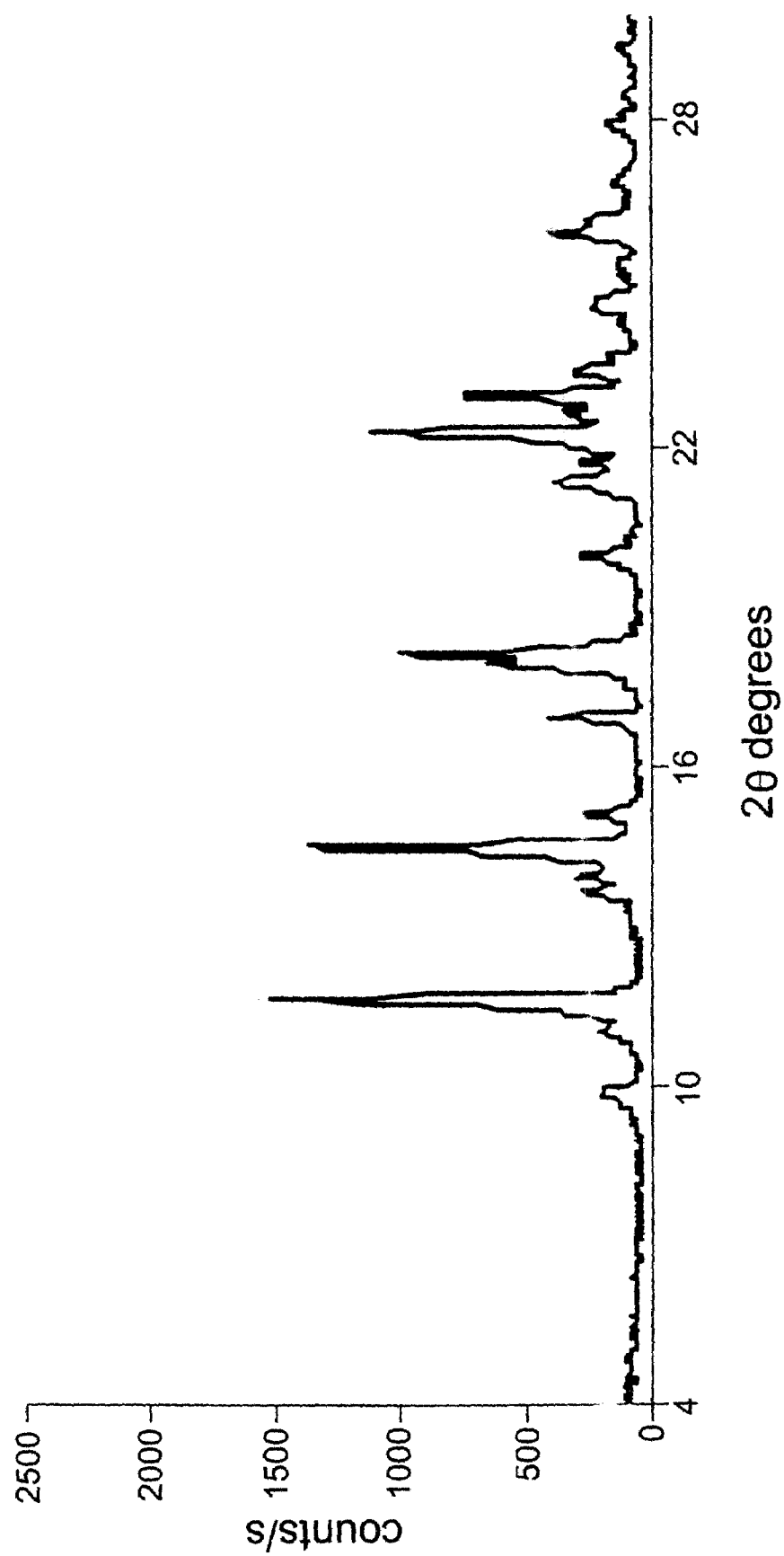
FIG. 1 represents a powder X-ray diffraction pattern of halobetasol propionate Form I.
Figure 2:
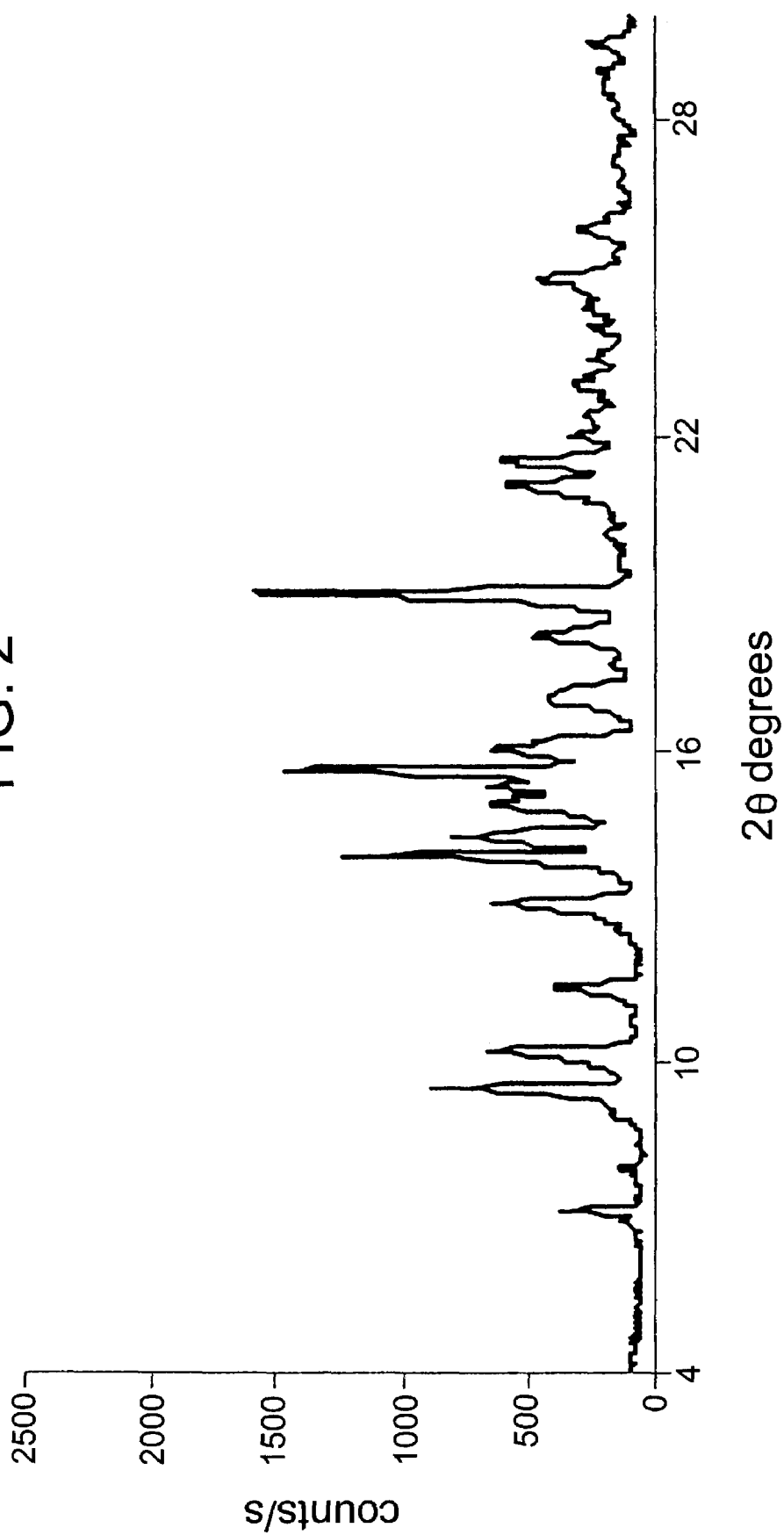
FIG. 2 represents a powder X-ray diffraction pattern of halobetasol propionate Form II.
Figure 3:
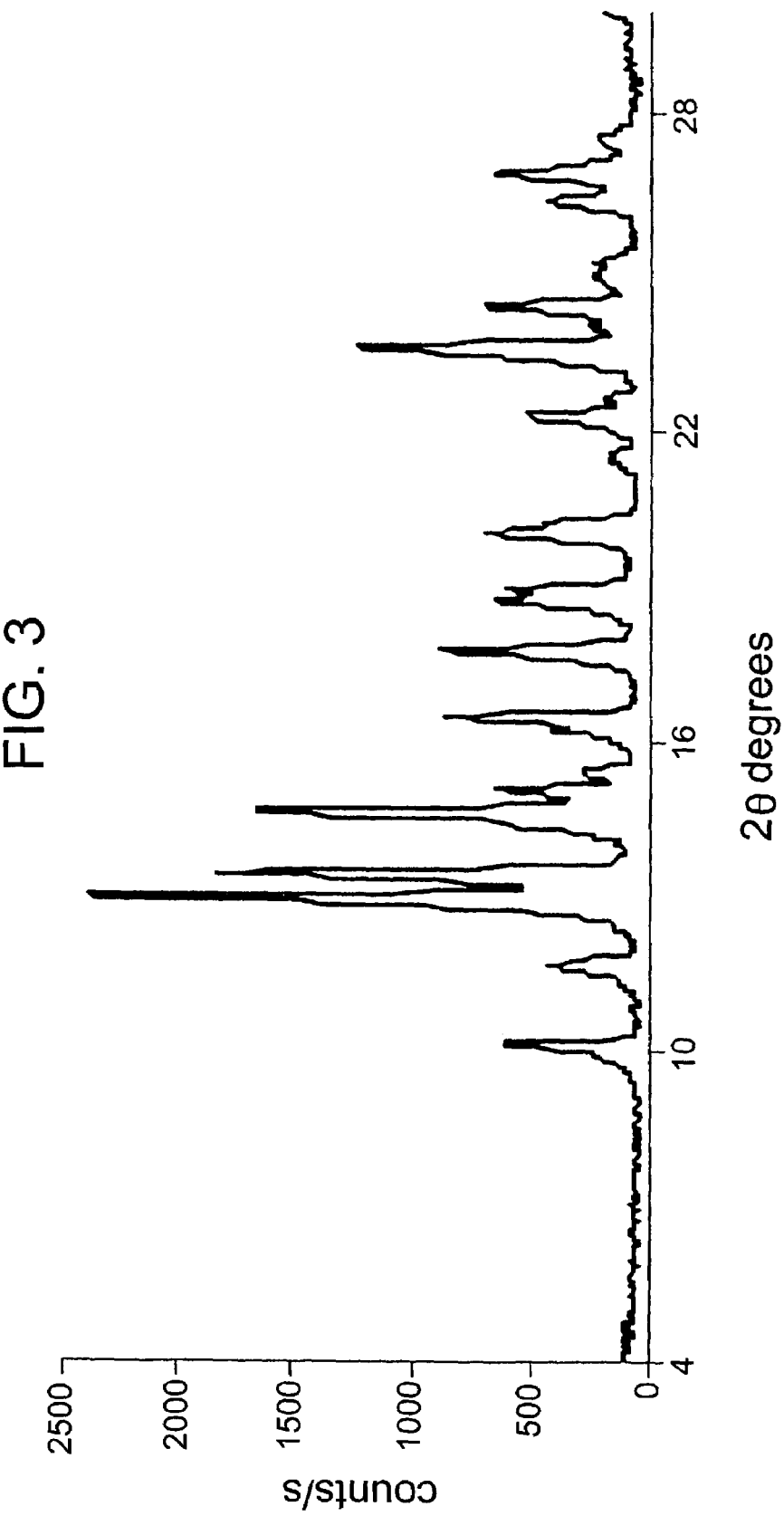
FIG. 3 represents a powder X-ray diffraction pattern of halobetasol propionate Form III.
Figure 4:
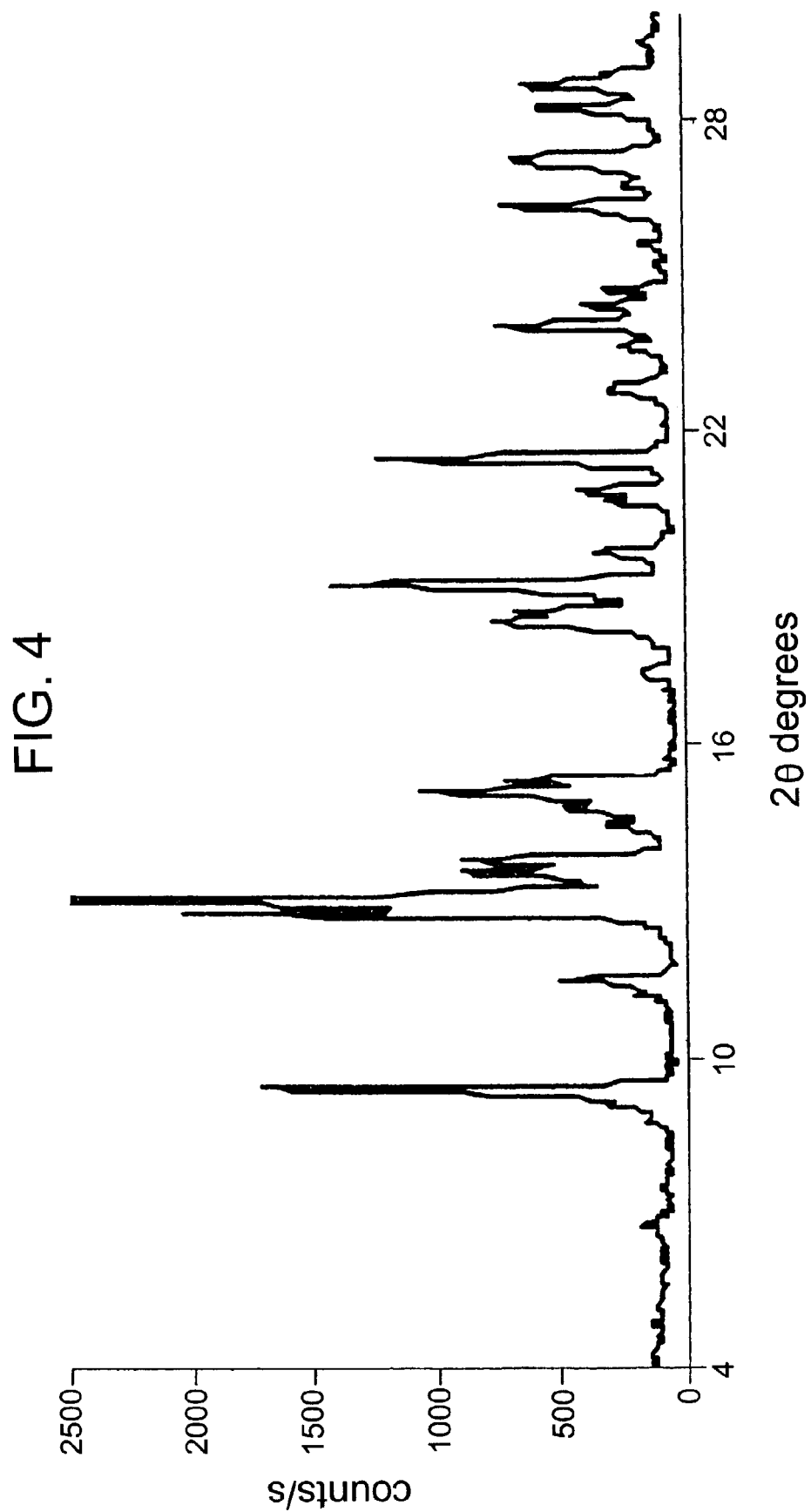
FIG. 4 represents a powder X-ray diffraction pattern of halobetasol propionate Form IV.
Figure 5:
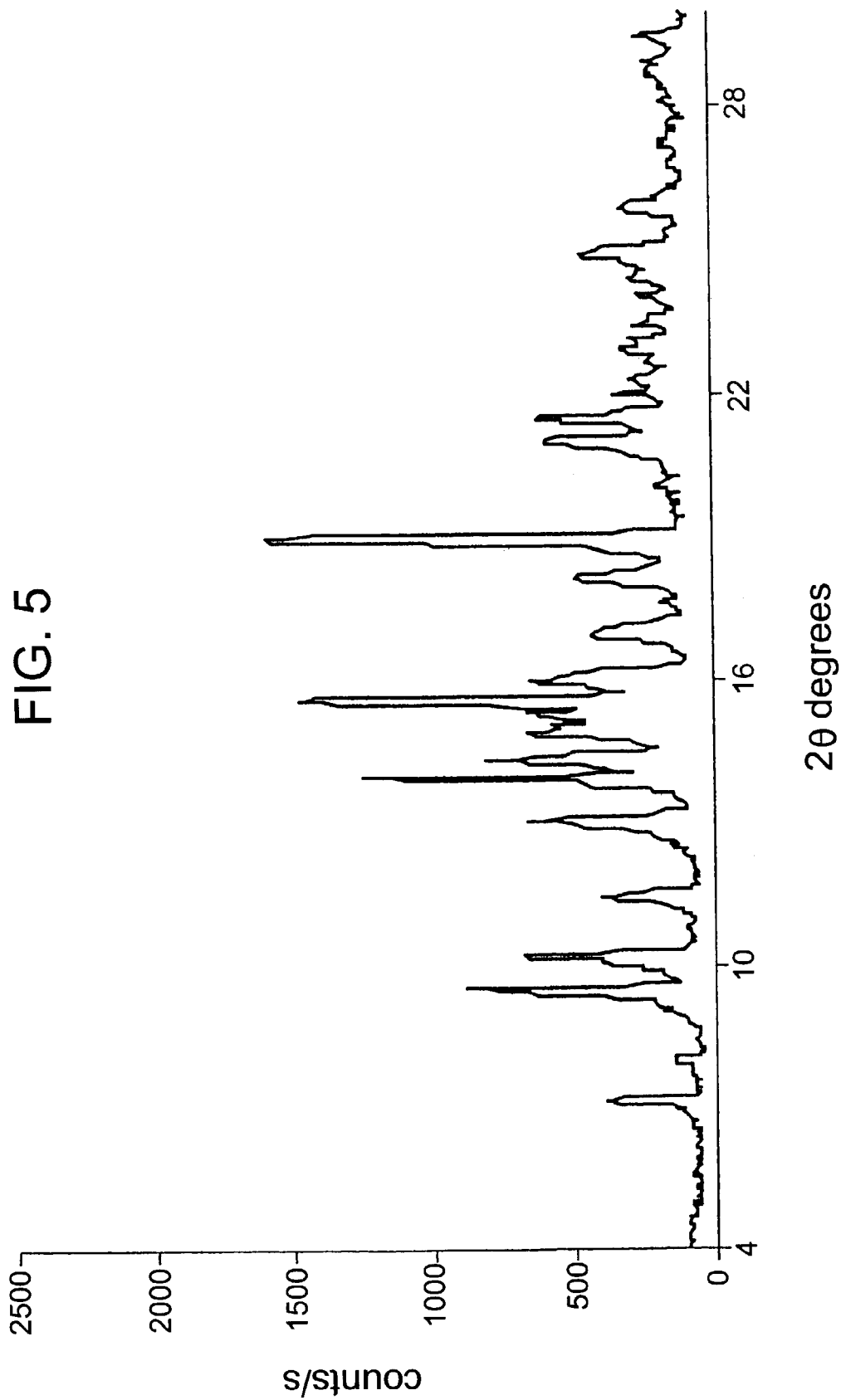
FIG. 5 represents a powder X-ray diffraction pattern of mixture of halobetasol propionate Form II and halobetasol propionate Form V.
Figure 6:
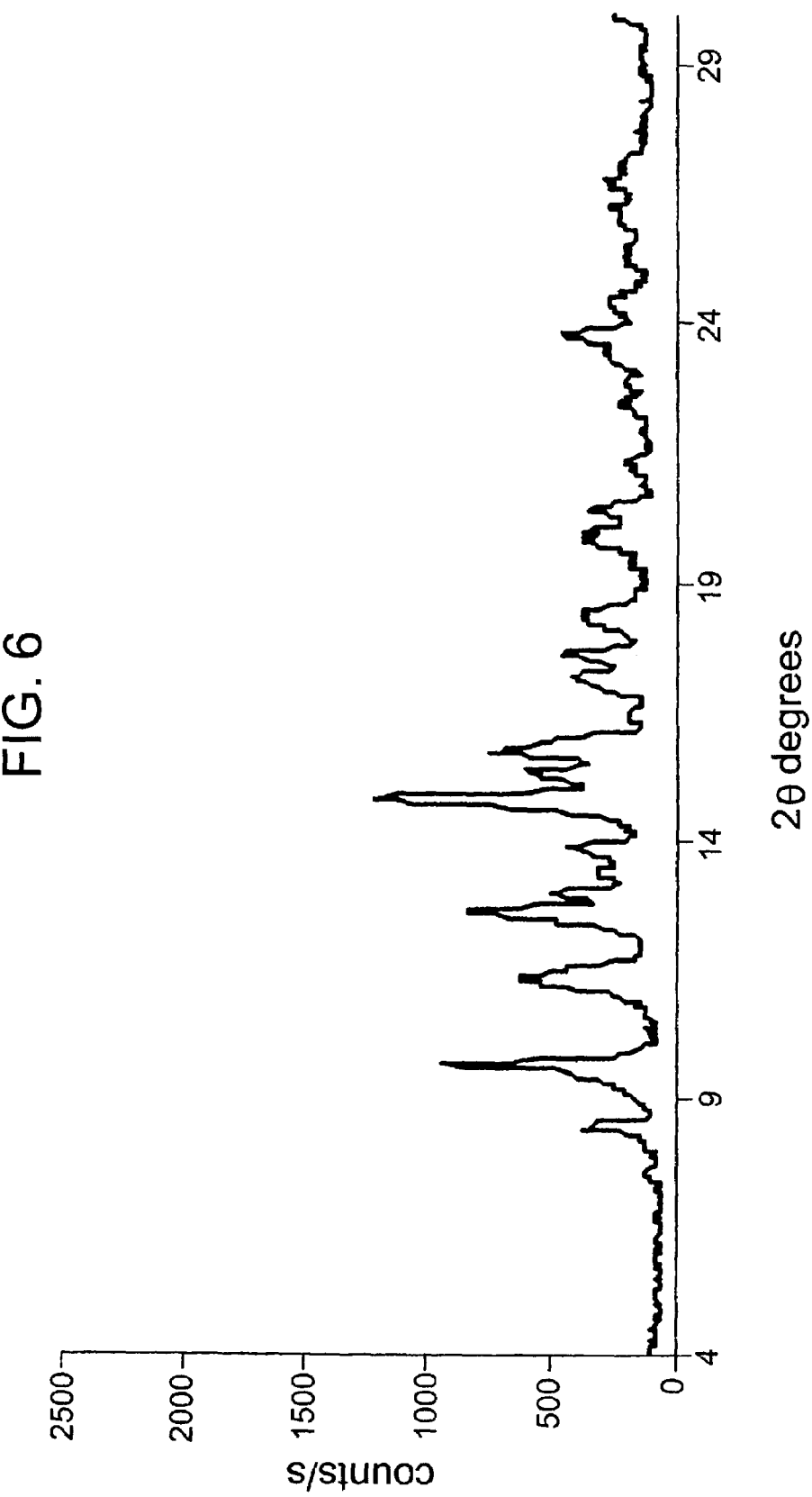
FIG. 6 represents a powder X-ray diffraction pattern of halobetasol propionate Form VI.
Figure 7:
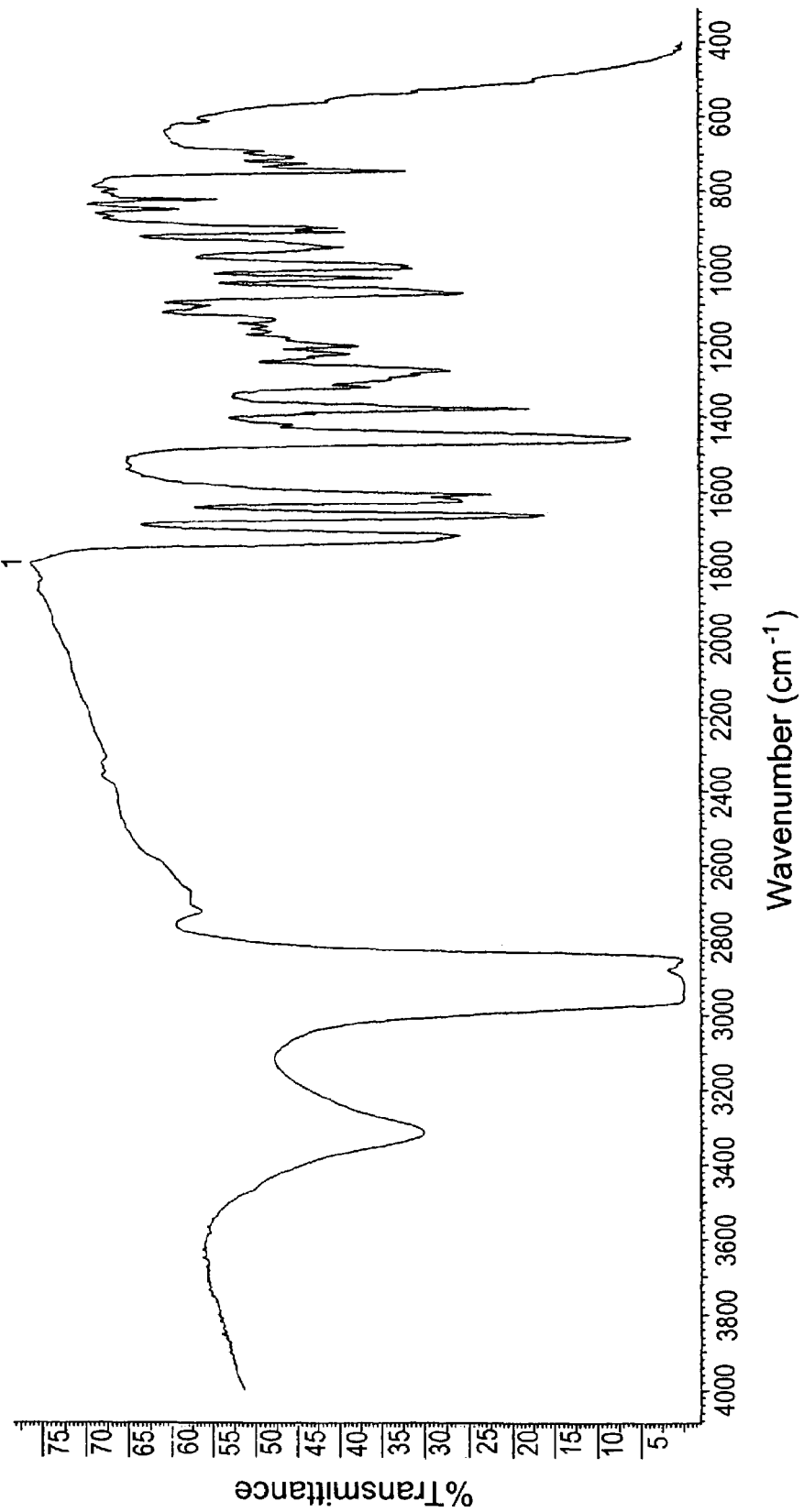
FIG. 7 represents an infra-red spectrum of halobetasol propionate Form I.
Figure 8:
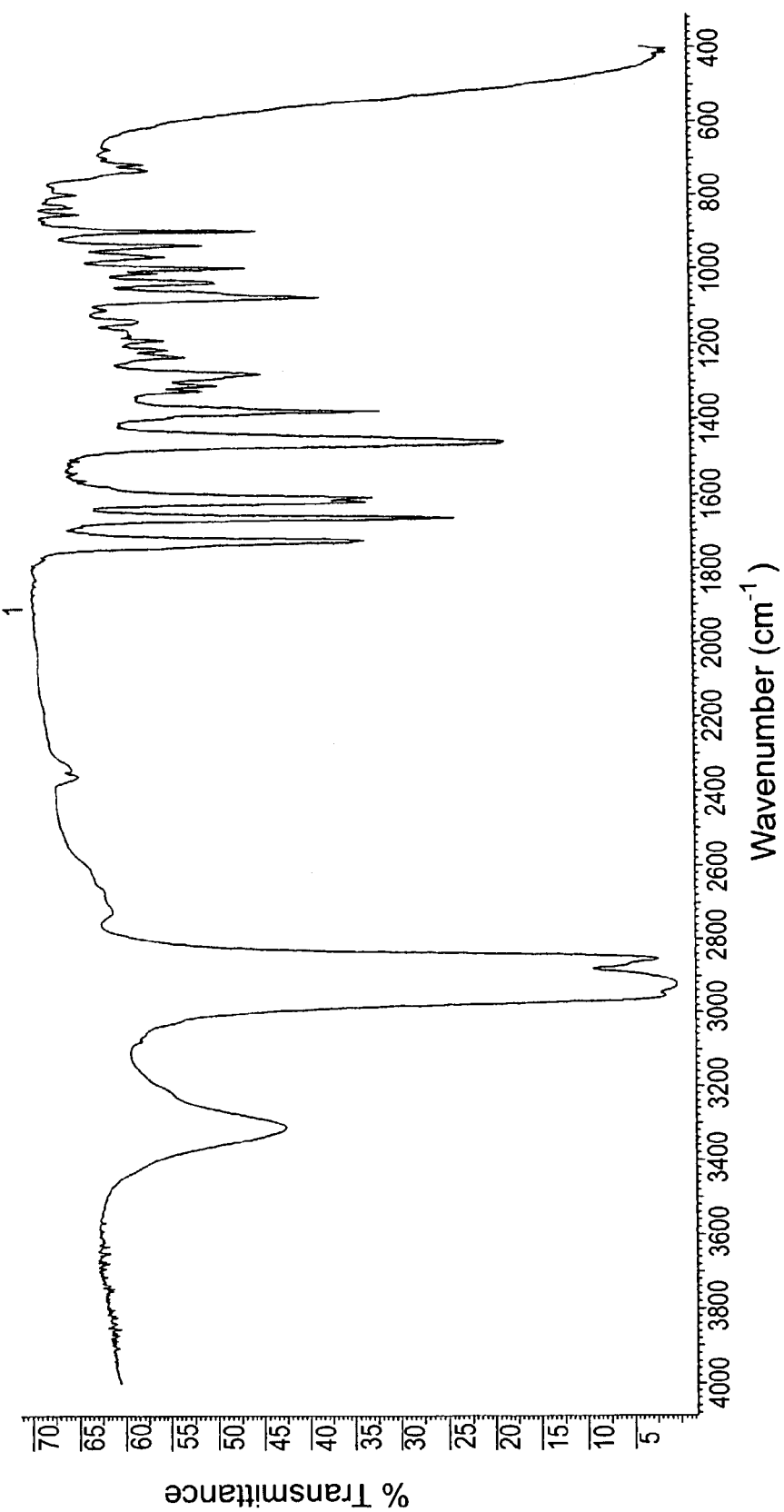
FIG. 8 represents an infra-red spectrum of halobetasol propionate Form II.
Figure 9:
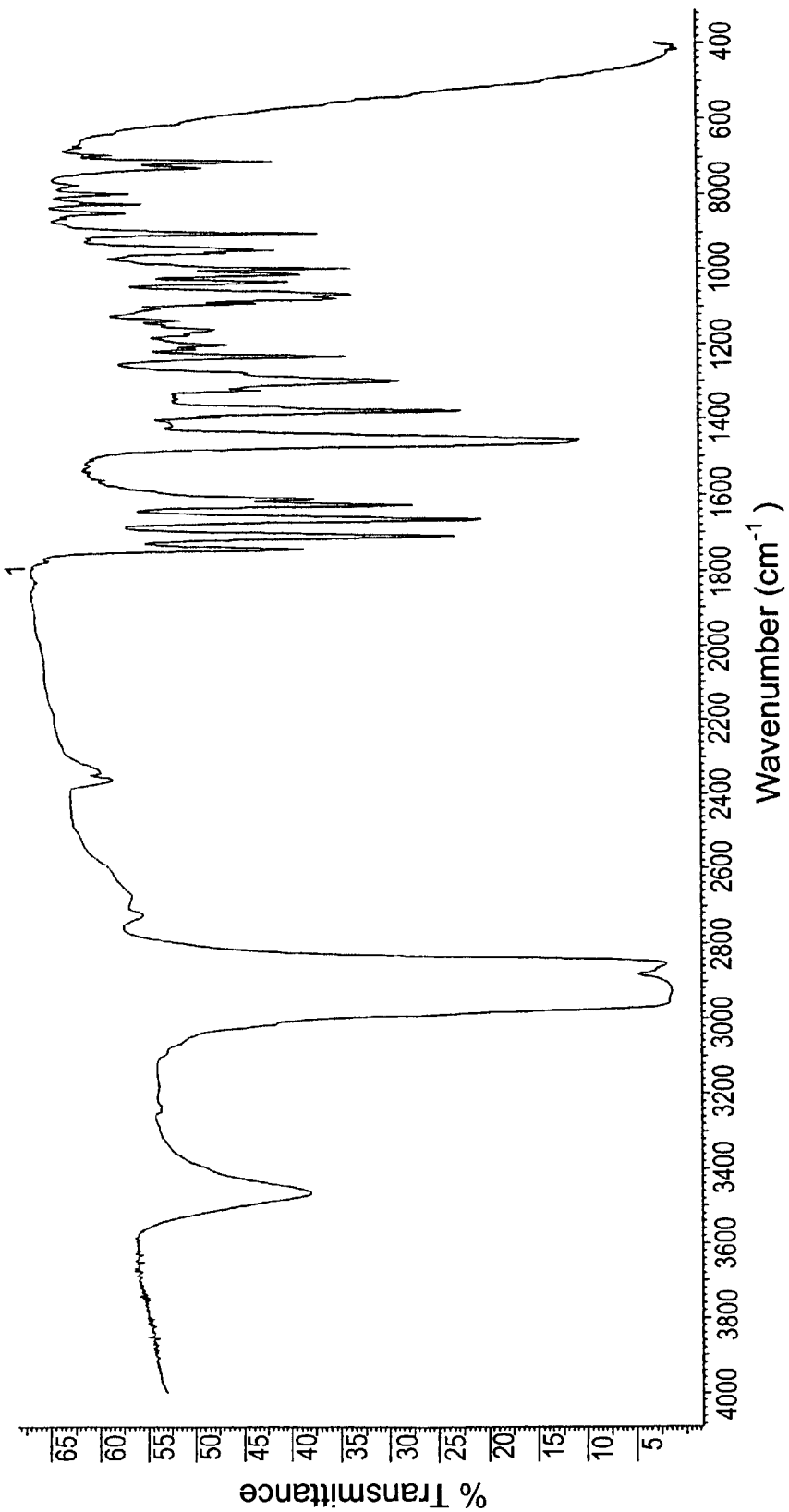
FIG. 9 represents an infra-red spectrum of halobetasol propionate Form III.
Figure 10:
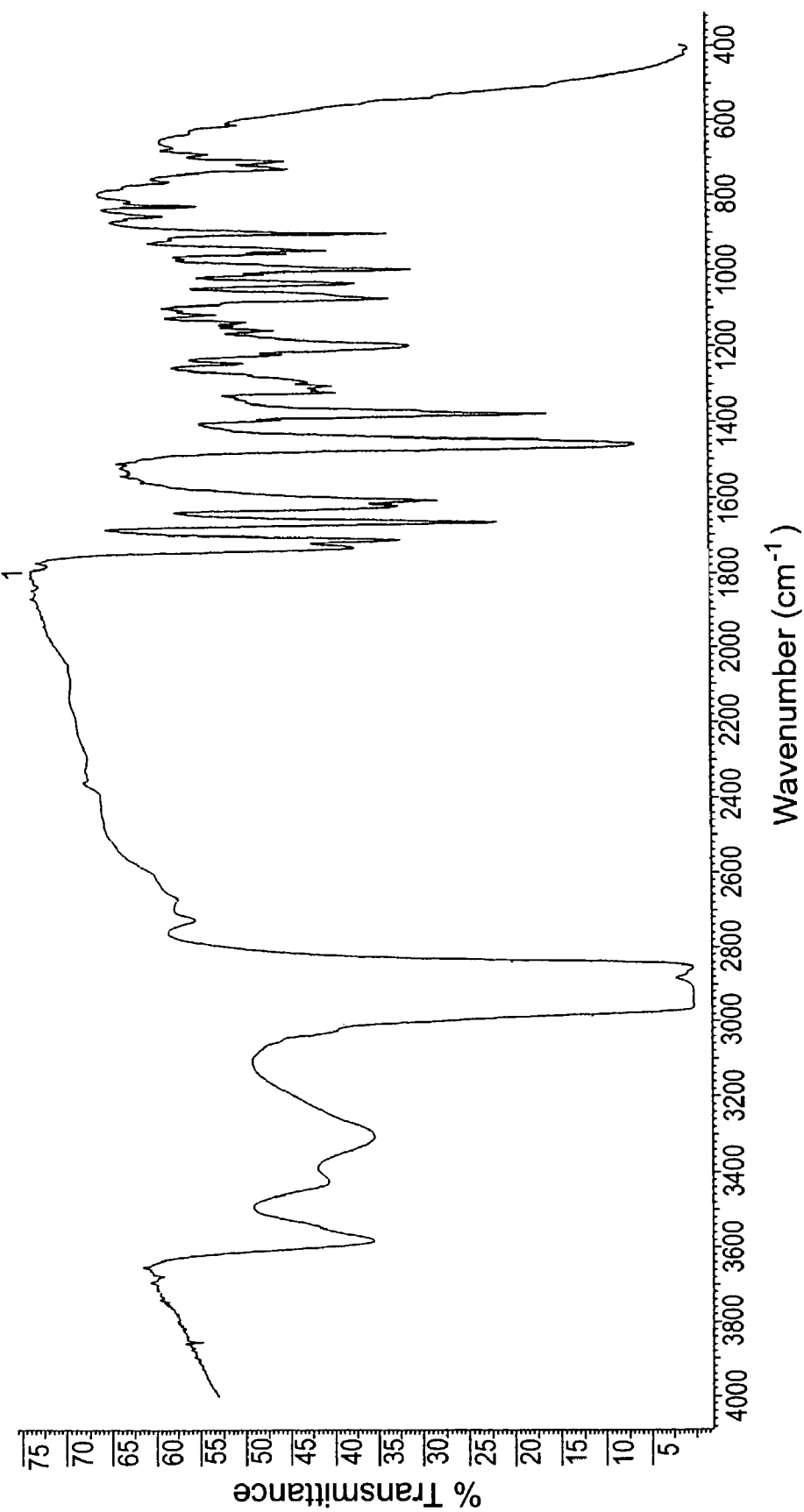
FIG. 10 represents an infra-red spectrum of halobetasol propionate Form IV.
Figure 11:
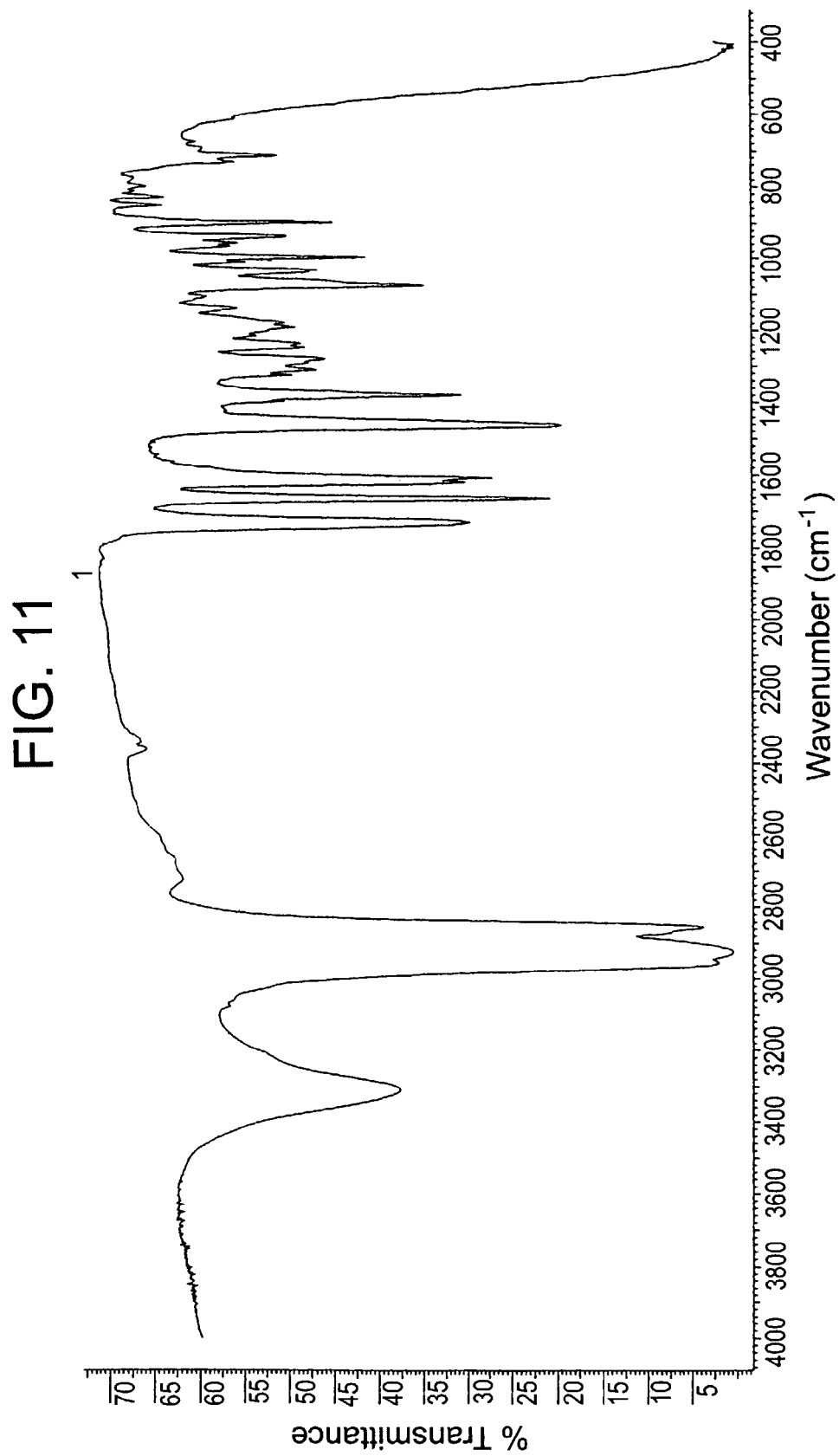
FIG. 11 represents an infra-red spectrum of mixture of halobetasol propionate Form II and halobetasol propionate Form V.
Figure 12:
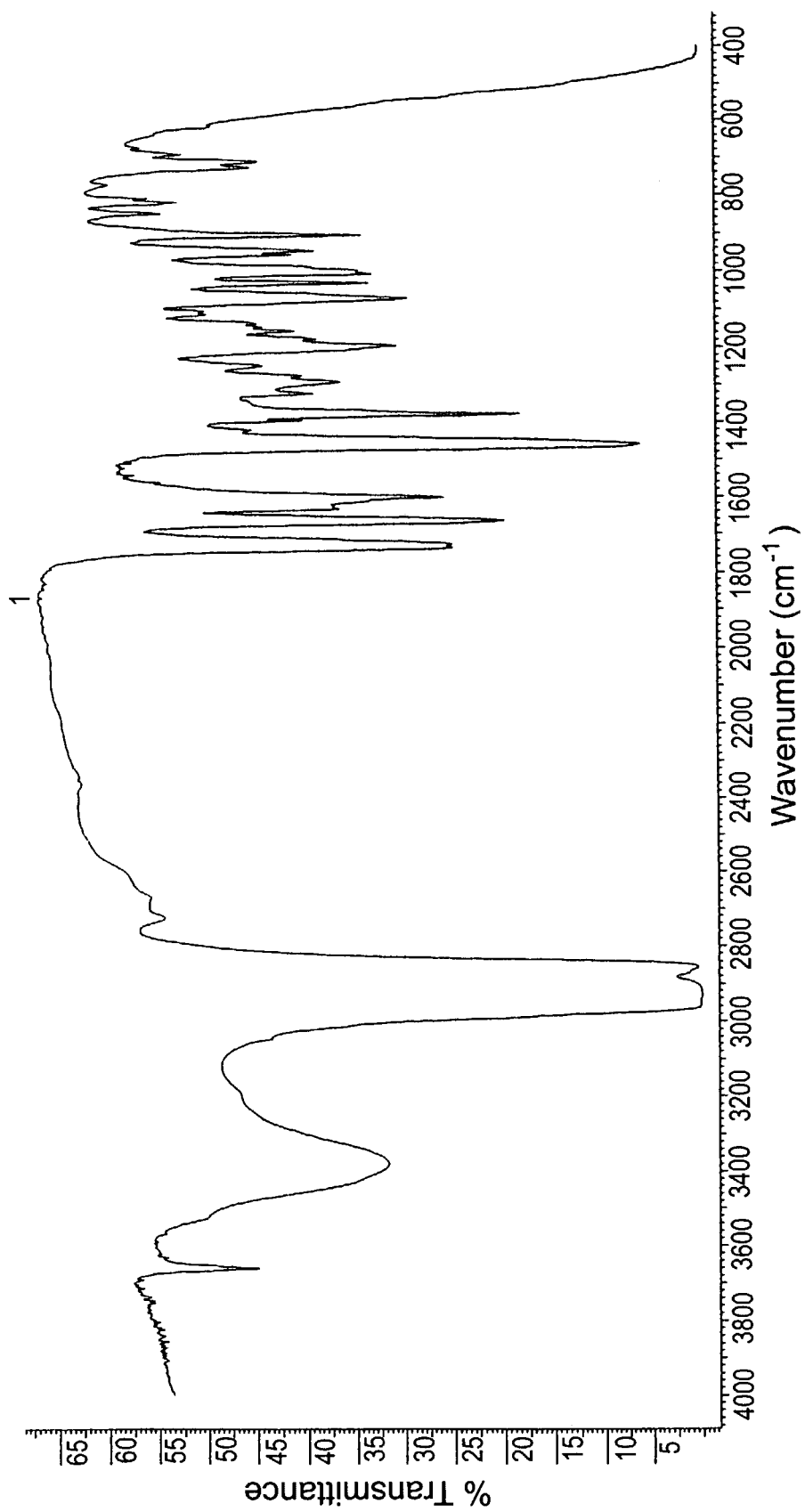
FIG. 12 represents an infra-red spectrum of halobetasol propionate Form VI.
Figure 13:
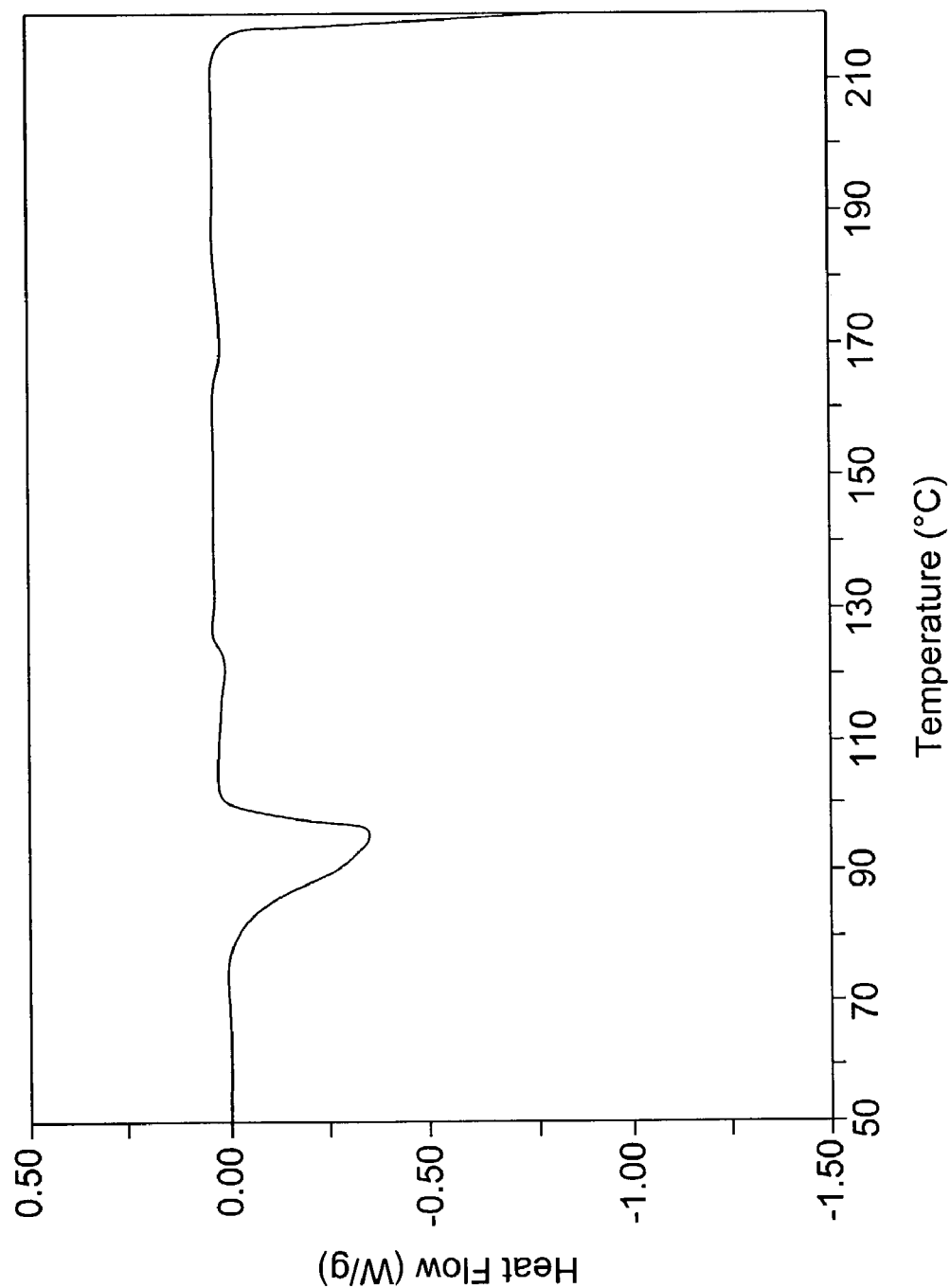
FIG. 13 represents a differential scanning calorimetry curve of halobetasol propionate Form I.
Figure 14:
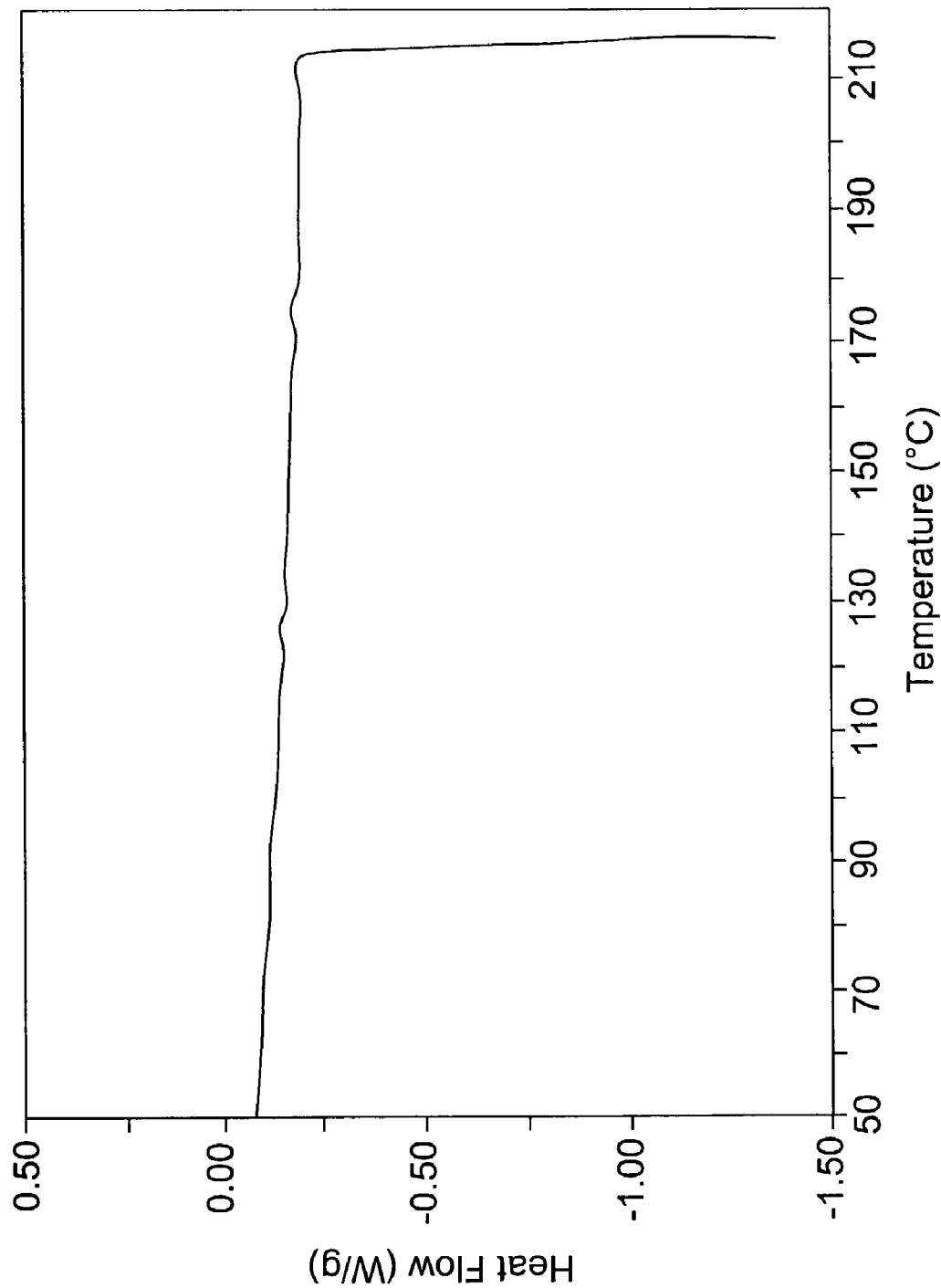
FIG. 14 represents a differential scanning calorimetry curve of halobetasol propionate Form II.
Figure 15:
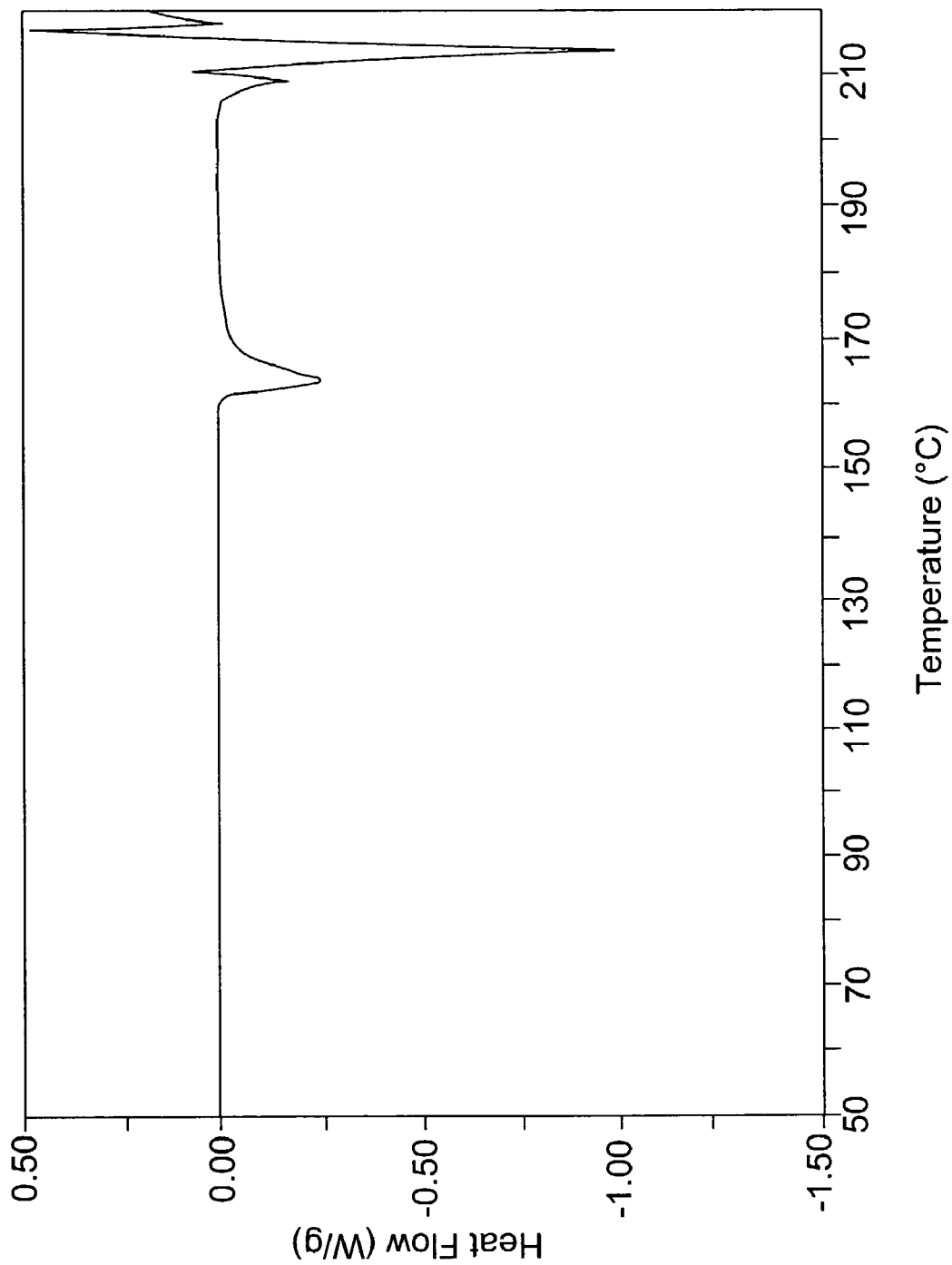
FIG. 15 represents a differential scanning calorimetry curve of halobetasol propionate Form III.
Figure 16:
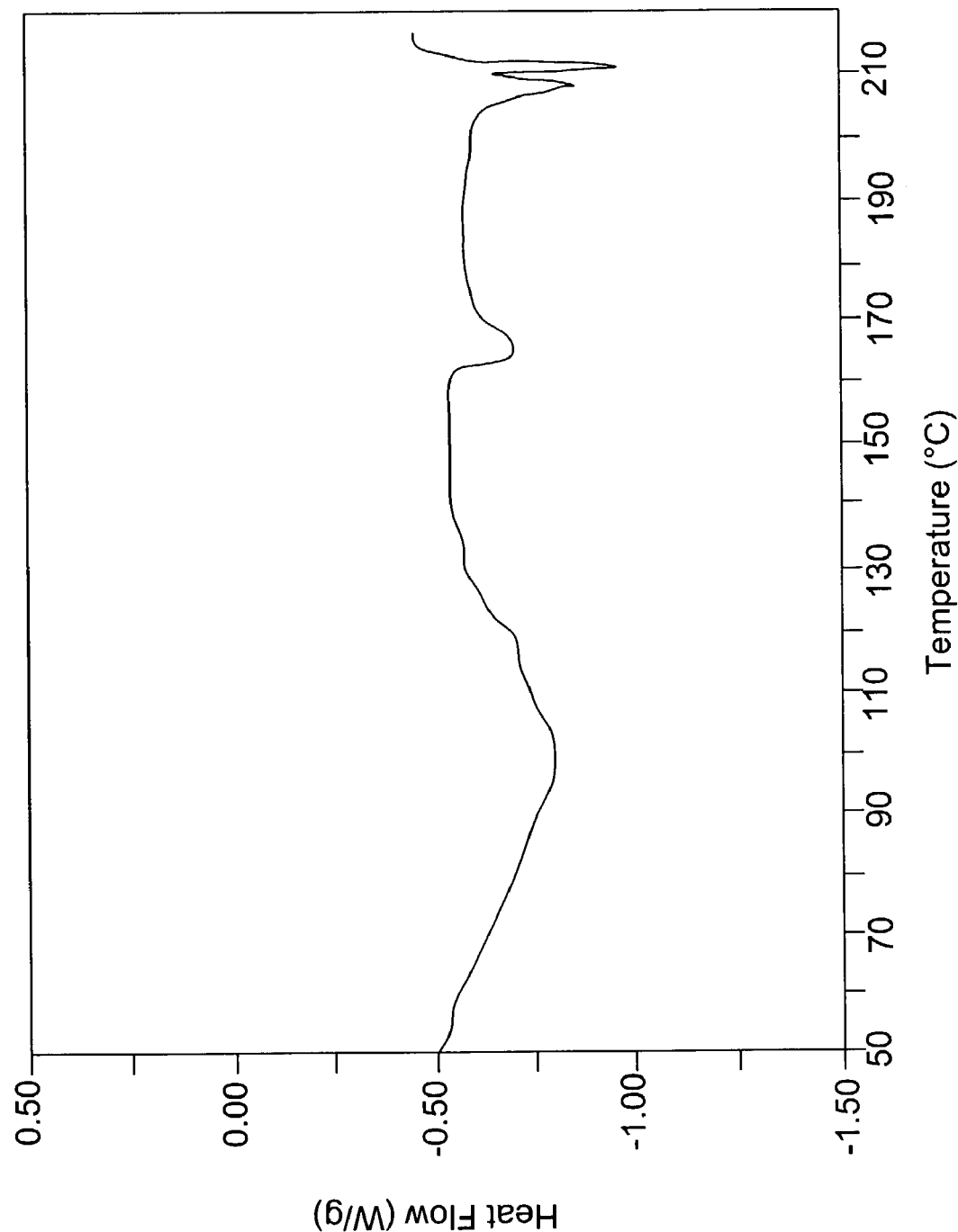
FIG. 16 represents a differential scanning calorimetry curve of halobetasol propionate Form IV.
Figure 17:
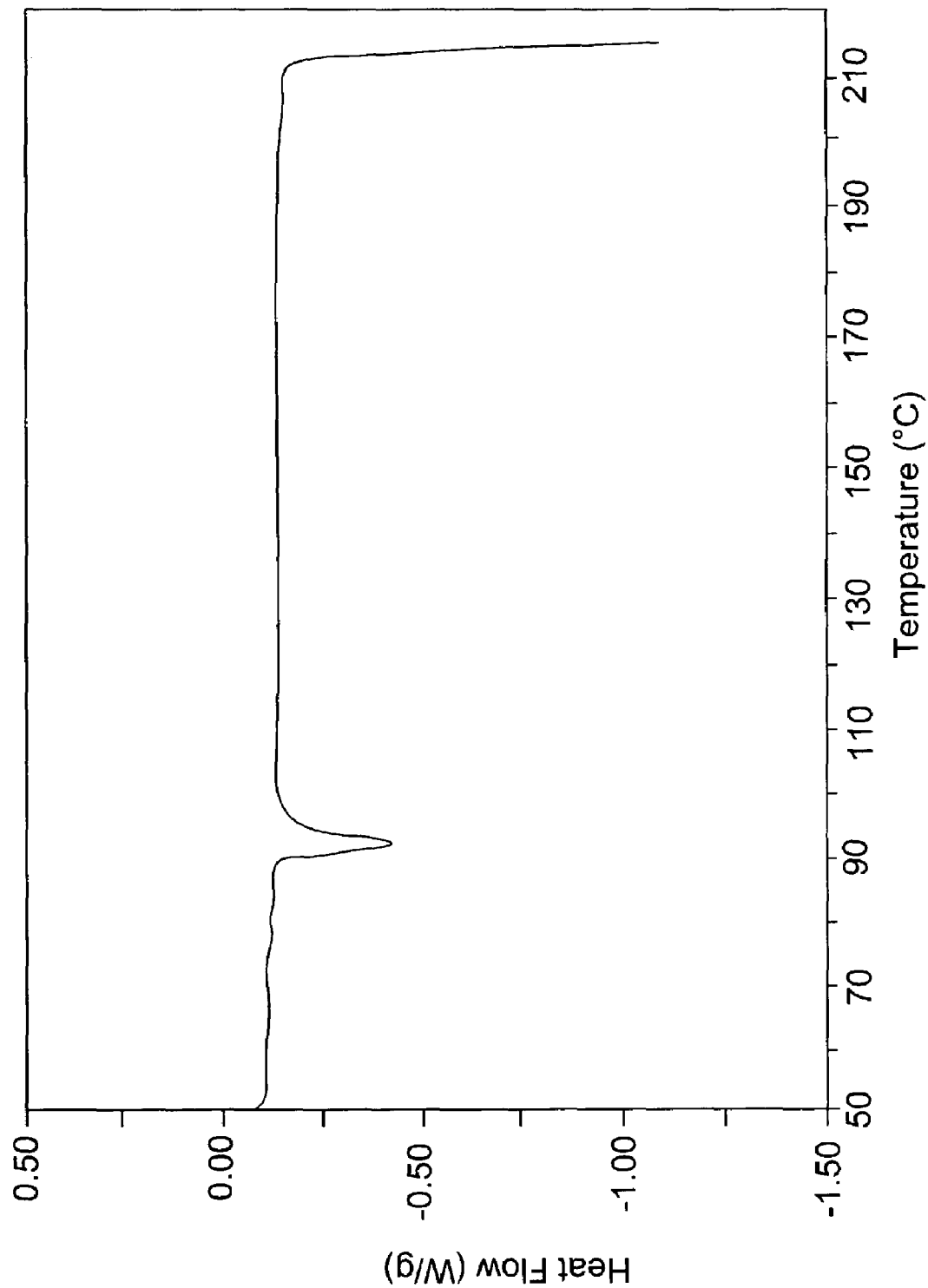
FIG. 17 represents a differential scanning calorimetry curve of mixture of halobetasol propionate Form II and halobetasol propionate Form V.
Figure 18:
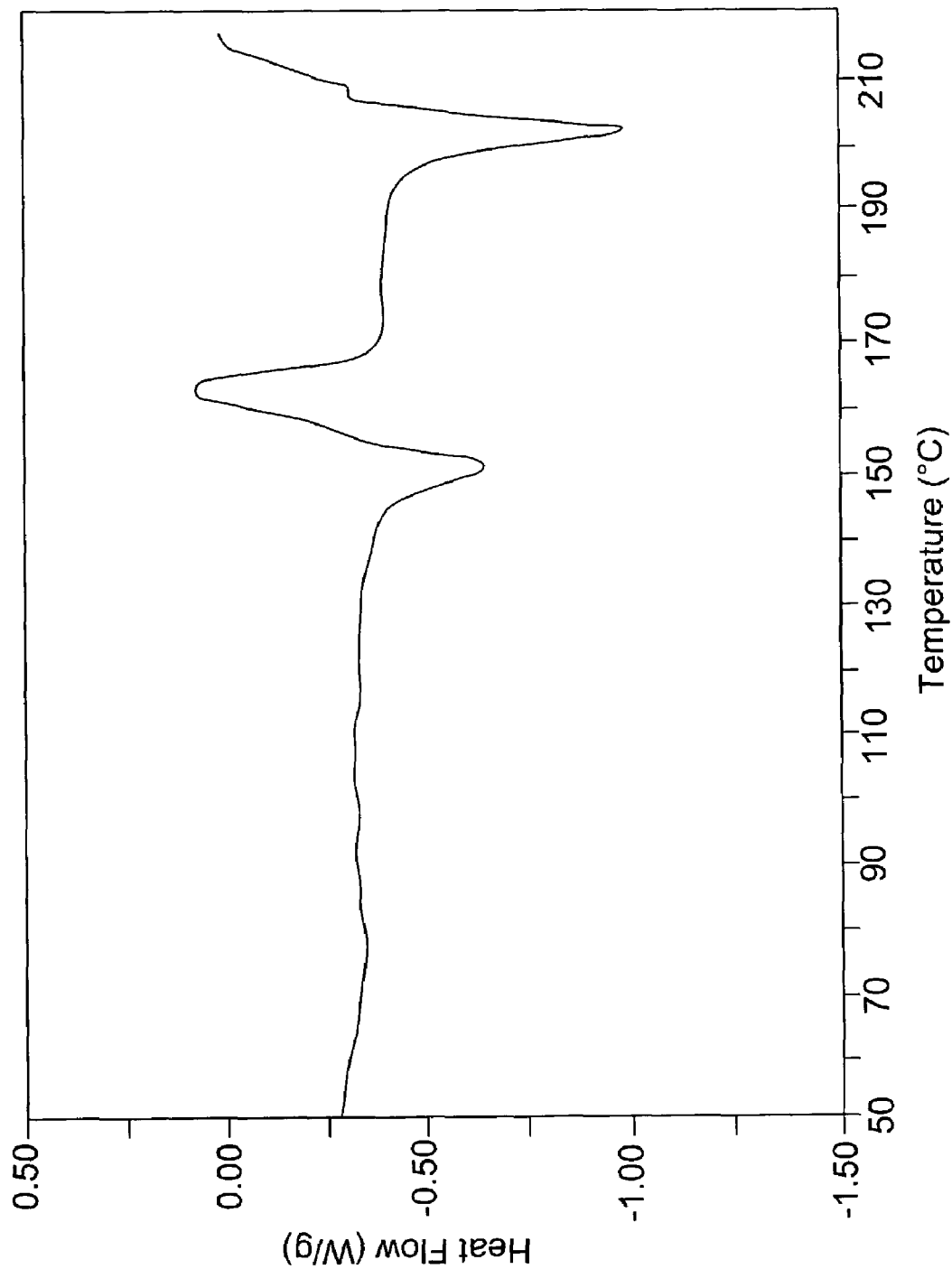
FIG. 18 represents a differential scanning calorimetry curve of halobetasol propionate Form VI.

In a three necked round bottom flask equipped with a reflux condenser, a thermometer and a magnetic stirrer, halobetasol propionate (1 gr) was dissolved in 8 ml of boiling mixture of methylene chloride/diethylether (5:1). The solution was maintained at reflux during few minutes, and left at room temperature to cool down to 25° C. The resulting crystals (0.92 gr) were filtered and dried during one hour at 50° C. in vacuum.

Example 2

Preparation of Halobetasol Propionate Form II

In a three necked round bottom flask equipped with a reflux condenser, a thermometer and a magnetic stirrer, halobetasol propionate (1 gr) was dissolved in 8 ml of boiling toluene. The solution was maintained at reflux during few minutes, and left at room temperature to cool down down to 25° C. The resulting crystals (0.95 gr) were filtered and dried during one hour at 50° C. in vacuum.

Example 3

Preparation of Halobetasol Propionate Form II

In a three necked round bottom flask equipped with a reflux condenser, a thermometer and a magnetic stirrer, halobetasol propionate. (1 gr) was dissolved in 8 ml of boiling toluene. The solution was maintained at reflux during few minutes, and left inside hot mineral oil for slow cooling, until the oil cooled down to 25° C. The resulting crystals (0.95 gr) were filtered and dried during one hour at 50° C. in vacuum.

Example 4

Preparation of Halobetasol Propionate Form II

In a 20 ml scintillation vial, halobetasol propionate Form V (1 gr) was heated to 120° C. during 10 minutes.

Example 5

Preparation of Halobetasol Propionate Form II

In a 20 ml scintillation vial, halobetasol propionate Form VI (1 gr) was heated to 180° C. during 10 minutes.

Example 6

Preparation of Halobetasol Propionate Form III

In a three necked round bottom flask equipped with a reflux condenser, a thermometer and a magnetic stirrer, halobetasol propionate (1 gr) was dissolved in 3 ml of boiling isopropanol. The solution was maintained at reflux during few minutes, and left to cool down to 25° C. Alternatively, the solution was cooled to 0° C. by dipping the flask in ice. The resulting crystals (0.90 gr) were filtered and dried one hour at 50° C. in vacuum.

Example 7

Preparation of Halobetasol Propionate Form III

In a three necked round bottom flask equipped with a reflux condenser, a thermometer and a magnetic stirrer, halobetasol propionate (1 gr) was dissoloved in 1 ml of boiling acetone. The solution was maintained at reflux during few minutes, and left to cool to 25° C. The resulting crystals (0.95 gr) were filtered and dried one hour at 50° C. in vacuum.

Example 8

Preparation of Halobetasol Propionate Form III

In a three neck round bottom flask equipped with a reflux condenser, a thermometer and a magnetic stirrer, halobetasol propionate (1 gr) was dissolved in 10 ml of boiling methylene chloride. The solution was maintained at reflux during few minutes, and then evaporated using a rotary evaporator. The resulting solid was dried in high vacuum at room temperature.

Example 9

Preparation of Halobetasol Propionate Form III

In a 20 ml scintillation vial, halobetasol propionate Form I (1 gr) was heated to 140° C. during 10 minutes.

Example 10

Preparation of Halobetasol Propionate Form III

In a 20 ml scintillation vial, halobetasol propionate Form IV (1 gr) was heated to 120° C. during 10 minutes.

Example 11

Preparation of Halobetasol Propionate Form IV

In a three neck round bottom flask equipped with a reflux condenser, a thermometer and a magnetic stirrer, halobetasol propionate (1 gr) was dissolved in 10 ml of boiling methanol. The solution was maintained at reflux during few minutes, and then 2 ml of water was added dropwise. The solution was cooled slowly to room temperature during 3 hours. The resulting crystals (0.7–0.8 gr) were dried during one hour at 50° C. in vacuum.

Example 12

Preparation of Halobetasol Propionate Form V

In a three necked round bottom flask equipped with a reflux condenser, a thermometer and a magnetic stirrer, halobetasol propionate (1 gr) was dissolved in 3 ml of boiling ethylacetate. The solution was maintained at reflux during few minutes, and left to cool to 25° C. The resulting crystals (0.85 gr) were filtered and dried during one hour at 50° C. in vacuum.

Example 13

Preparation of Halobetasol Propionate Form VI

In a three necked round bottom flask equipped with a reflux condenser, a thermometer and an magnetic stirrer, halobetasol propionate (1 gr) was dissolved in 10 ml of boiling methanol. The solution was maintained at reflux during few minutes, and left to cool to 25° C. The resulting crystals (0.85 gr) were filtered and dried during one hour at 50° C. in vacuum.

Example 14

Preparation of Halobetasol Propionate Ointment 0.05%

| Ingredients: | |
|---|---|
| Halobetasol propionate | 0.05% |
| White petrolatum USP | 79.95% |
| Dehymuls E | 7.5% |
| White wax NF | 5% |
| Propylene glycol USP | 7.5% |

Procedure:

Component A: Heat to 70° C. and mix together white petrolatum NF, Dehymuls E and white wax NF.

Component B: Heat propylene glycol USP to 70° C. and add with high shear mixing halobetasol propionate to dissolution.

Using a high shear mixer add, under vacuum, component B to component A. Cool the product.

Example 15

Preparation of Halobetasol Propionate Cream 0.05%

| Ingredients: | |
|---|---|
| Halobetasol propionate | 0.05% |
| Cetyl alcohol NF | 6% |
| Isopropyl isostearate | 3% |
| Isopropyl palmitate NF | 2% |
| Steareth 21 | 3% |
| Germall II | 0.2% |
| Glycerin 99.5% USP | 2% |
| Kathon CG | 0.05% |
| Purified water (part A) | 78.7% |
| Purified water (part B) | 5% |

Procedure:

Component A: Heat to 70° C. and mix cetyl alcohol NF, isopropyl isostearate, isopropyl palmitate NF and Steareth 21.

Component B: Heat to 70° C. and mix purified water (part A) and Germall II.

Component C: With high shear mixing mix glycerin, Kathon CG and halobetasol propionate. Then add gradually purified water (part B).

Using a high shear mixer mix component A to component B. Adjust temperature to 40° C.

Add the component C, using a high shear mixer, to the combined components A and B. Cool.

Example 16

Preparation of Halobetasol Propionate Emollient Ointment 0.05%

| Ingredients: | |
| --- | --- |
| Halobetasol propionate | 0.05% |
| Softisan 378 | 71.95% |
| Propylene glycol monostearate | 8% |
| Castor oil | 15% |
| Oleyl alcohol | 5% |

Procedure:

Heat together oleyl alcohol and castor oil to 60° C. Add halobetasol propionate. Mix to dissolution.

Separately heat Softisan 378 and propylene glycol monostearate to 55–60° C.

Add, under vacuum the second solution to the first. Cool.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. Halobetasol propionate having crystalline Form I that produces a powder X-ray diffraction pattern with reflections at 9.9, 11.0, 11.6, 13.6, 14.0, 14.5, 15.1, 16.9, 17.9, 18.1, 19.9, 21.1, 21.3, 21.7, 22.3, 22.6, 23.0, 23.4, 23.7, 24.5, 24.7 25.4, 25.9, 26.0, 26.9, 28.0, 28.6, and 29.4±0.2 degrees 2θ.

2. The crystalline halobetasol propionate Form I as described in claim 1, further characterized by an infra-red spectrum with strong absorption peaks at 1607, 1627, 1666, 1715, and 1733±4 cm−1.

3. A process for preparing crystalline halobetasol propionate Form. I of claim 1, comprising a step of crystallization from methylene chloride: diethylether mixture.

4. Halobetasol propionate having crystalline Form II that produces a powder X-ray diffraction pattern with reflections at 8.0, 10.2, 11.4, 13.0, 14.9, 16.1, 17.1, 18.2, 19.6, 21.0, 22.0, 22.3, 23.1, 24.1, 25.0, 25.9, 27.3, 28.2, 28.5, and 29.0±0.2 degrees 2θ.

5. The crystalline halobetasol propionate Form II as described in claim 4, further characterized by an infra-red spectrum with strong absorption peaks at 1607, 1618, 1662 and 1723±4 cm−1.

6. The crystalline halobetasol propionate Form II as described in claim 4, further characterized by a melting point of 214.5–215.0° C.

7. A process for preparing crystalline halobetasol propionate Form II of claim 4, comprising a step of crystallization from toluene.

8. A process for preparing halobetasol propionate Form II claim 4, comprising a step of heating Form V.

9. A process for preparing crystalline halobetasol propionate Form II of claim 4, comprising a step of heating Form VI.

10. Halobetasol propionate having crystalline Form III that produces a powder X-ray diffraction pattern with reflections at 7.0, 10.1, 11.7, 13.0, 13.5, 14.6, 15.1, 15.5, 16.2, 16.5, 17.7, 18.7, 19.0, 20.0, 20.2, 21.6, 22.3, 22.6, 23.6, 24.4, 24.9, 25.3, 26.4, 26.9, 27.5, and 30.3±0.2 degrees 2θ.

11. The crystalline halobetasol propionate Form III as described in claim 10, further characterized by an infra-red spectrum with strong absorption peaks at 1611, 1627, 1665, 1708, and 1742±4 cm−1.

12. The crystalline halobetasol propionate Form III as described in claim 10, further characterized by a melting point of 205.8–209° C.

13. A process for preparing crystalline halobetasol propionate Form III of claim 10, comprising a step of crystallization from isopropanol, acetone, or methylene chloride.

14. A process for preparing crystalline halobetasol propionate Form III of claim 10, comprising a step of heating Form I.

15. A process for preparing crystalline halobetasol propionate Form III of claim 10, comprising a step of heating Form IV.

16. Halobetasol propionate having crystalline Form IV that produces a powder X-ray diffraction pattern with reflections at 6.7, 9.4, 11.5, 12.8, 13.1, 13.6, 13.8, 14.5, 14.8, 15.1, 15.4, 17.4, 18.3, 18.6, 19.1, 19.7, 20.7, 20.9, 21.5, 22.8, 23.6, 24.0, 24.4, 24.7, 25.2, 25.6, 26.4, 26.7, 27.2, 28.2, 28.7 and 28.9±0.2 degrees 2θ.

17. The crystalline halobetasol propionate Form IV as described in claim 16, further characterized by an infra-red spectrum with strong absorption peaks at 1606, 1621, 1664, 1711 and 1727±4 cm−1, and three broad hydroxyl absorption peaks at 3304, 3425 and 3580±4 cm−1.

18. A process for preparing crystalline halobetasol propionate form IV of claim 16, comprising a step of crystallization from a methanol-water mixture.

19. Halobetasol propionate having crystalline Form V that produces a powder X-ray diffraction pattern with reflections at 7.2, 8.5, 9.0, 9.5, 10.8, 14.0, 14.3, 15.3, 15.6, 16.2, 16.9, 17.7, 19.0, 20.1, 21.5, 22.9, 23.5, 23.6, 24.4, 25.4, 26.0, 26.9, 27.2, and 29.5 ±0.2 degrees 2θ.

20. A process for preparing crystalline halobetasol propionate Form V of claim 19, comprising a step of crystallization from ethyl acetate.

21. Halobetasol propionate having crystalline Form VI that produces a powder X-ray diffraction pattern with reflections at 8.5, 9.2, 9.7, 10.0, 11.3, 11.6, 12.6, 13.0, 13.4, 13.9, 14.8, 15.3, 15.7, 16.0, 16.4, 16.9, 17.2, 17.6, 18.2, 18.5, 19.4, 19.8, 20.0, 20.4, 21.2, 21.4, 22.3, 22.5, 22.9, 23.4, 23.8, 24.3, 24.4, 25.1, 25.3, 25.5, 25.9, 26.2, 26.7, and 27.2±0.2 degrees 2θ.

22. The crystalline halobetasol propionate Form VI as described in claim 21, further characterized by an infra-red spectrum with strong absorption peaks at 1600, 1614, 1623, 1633, 1664, 1725 and 1735±4 cm−1, and two hydroxyl absorption peaks at 3659 (narrow) and 3378 (broad)±4 cm−1.

23. A process for preparing crystalline halobetasol propionate Form VI of claim 21, comprising a step of crystallization from methanol.

24. Stable topical pharmaceutical compositions comprising at least one of the crystalline halobetasol propionate of Forms I-VI as defined in any one of claims 1, 4, 10, 16, 19, or 21 as active ingredient therein in combination with a pharmaceutically acceptable carrier.

25. The crystalline halobetasol propionate of claim 1 having crystalline Form I, substantially free of crystalline forms of halobetasol propionate other than Form I.

26. The crystalline halobetasol propionate of claim 4 having crystalline Form II, substantially free of crystalline forms of halobetasol propionate other than Form II.

27. The crystalline halobetasol propionate of claim 10 having crystalline Form III, substantially free of crystalline forms of halobetasol propionate other than Form III.

28. The crystalline halobetasol propionate of claim 16 having crystalline Form IV, substantially free of crystalline forms of halobetasol propionate other than Form IV.

29. The crystalline halobetasol propionate of claim 19 having crystalline Form V, substantially free of crystalline forms of halobetasol propionate other than Form V.

30. The crystalline halobetasol propionate of claim 21 having crystalline Form VI, substantially free of crystalline forms of halobetasol propionate other than Form VI.

31. A stable topical pharmaceutical composition comprising, as the active ingredient, the crystalline halobetasol propionate of claim 25.

32. A stable topical pharmaceutical composition comprising, as the active ingredient, the crystalline halobetasol propionate of claim 26.

33. A stable topical pharmaceutical composition comprising, as the active ingredient, the crystalline halobetasol propionate of claim 27.

34. A stable topical pharmaceutical composition comprising, as the active ingredient, the crystalline halobetasol propionate of claim 28.

35. A stable topical pharmaceutical composition comprising, as the active ingredient, the crystalline halobetasol propionate of claim 29.

36. A stable topical pharmaceutical composition comprising, as the active ingredient, the crystalline halobetasol propionate of claim 30.

* * * * *